United States Patent
Heibel et al.

(10) Patent No.: US 9,287,014 B2
(45) Date of Patent: Mar. 15, 2016

(54) THERMO-ACOUSTIC NUCLEAR POWER DISTRIBUTION MEASUREMENT ASSEMBLY

(71) Applicant: Westinghouse Electric Company LLC, Cranberry Township, PA (US)

(72) Inventors: Michael D. Heibel, Harrison City, PA (US); Robert W. Flammang, Pittsburgh, PA (US); David M. Sumego, New Brighton, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 47 days.

(21) Appl. No.: 14/330,010

(22) Filed: Jul. 14, 2014

(65) Prior Publication Data

US 2014/0362965 A1  Dec. 11, 2014

Related U.S. Application Data

(63) Continuation-in-part of application No. 13/869,159, filed on Apr. 24, 2013.

(51) Int. Cl.
*G21C 17/104* (2006.01)
*G21C 17/10* (2006.01)
(Continued)

(52) U.S. Cl.
CPC ............ *G21C 17/102* (2013.01); *G21C 17/108* (2013.01); *G21C 17/104* (2013.01); *G21C 17/112* (2013.01)

(58) Field of Classification Search
CPC .. G21C 17/102; G21C 17/104; G21C 17/108; G21C 17/112; G01H 3/00
USPC .......................................... 376/245, 247, 254
See application file for complete search history.

(56) References Cited

U.S. PATENT DOCUMENTS 2,486,845 A  * 11/1949  Herzog ...................... 250/336.1
3,897,271 A  *  7/1975  Kim .............................. 376/320
(Continued)

FOREIGN PATENT DOCUMENTS

JP      2009145332 A      7/2009

OTHER PUBLICATIONS

International Search Report and Written Opinion of the International Searching Authority for PCT/US2014/046506 dated Mar. 25, 2015 (Forms PCT/ISA/220, PCT/ISA/210, PCT/ISA/237).

*Primary Examiner* — Jack W Keith
*Assistant Examiner* — Daniel Wasil
(74) *Attorney, Agent, or Firm* — Joseph C. Spadacene; Westinghouse Electric Company LLC

(57) ABSTRACT

A nuclear power distribution measurement assembly that is sized to fit within an instrumentation thimble of a nuclear fuel assembly, that employs a spaced tandem arrangement of thermo-acoustic engines, each of which has a heat source side that is insulated from the reactor coolant traversing the nuclear core in which the fuel assembly is to be placed and a cold side housing a resonator chamber with enhanced thermal conductance to the coolant. The resonator chamber of each of the thermo-acoustic engines is of a different length to generate a different frequency whose amplitude is proportional to the neutron activity at the axial and radial position of the thermo-acoustic engine. The frequency identifies the measurement assembly's position. Acoustic telemetry is employed to monitor the acoustic waves generated by the individual thermo-acoustic engines to provide a remote reading of the axial and radial power distribution of a reactor core.

22 Claims, 4 Drawing Sheets

(51) Int. Cl.
*G21C 17/108* (2006.01)
*G21C 17/112* (2006.01)

(56) References Cited

U.S. PATENT DOCUMENTS

| | | | |
|---|---|---|---|
| 4,862,007 A * | 8/1989 | Mallory | 376/272 |
| 4,876,059 A * | 10/1989 | Conroy | 376/247 |
| 5,473,644 A * | 12/1995 | Yasuoka et al. | 376/254 |
| 5,490,184 A * | 2/1996 | Heibel | 376/254 |
| 6,252,923 B1 | 6/2001 | Iacovino et al. | |
| 2009/0135984 A1* | 5/2009 | Fawks et al. | 376/247 |
| 2010/0104060 A1* | 4/2010 | Koste et al. | 376/247 |
| 2011/0002432 A1 | 1/2011 | Heibel et al. | |
| 2012/0177166 A1* | 7/2012 | Seidel et al. | 376/254 |
| 2013/0177120 A1* | 7/2013 | Cheatham et al. | 376/219 |
| 2014/0050293 A1* | 2/2014 | Garrett et al. | 376/412 |

* cited by examiner

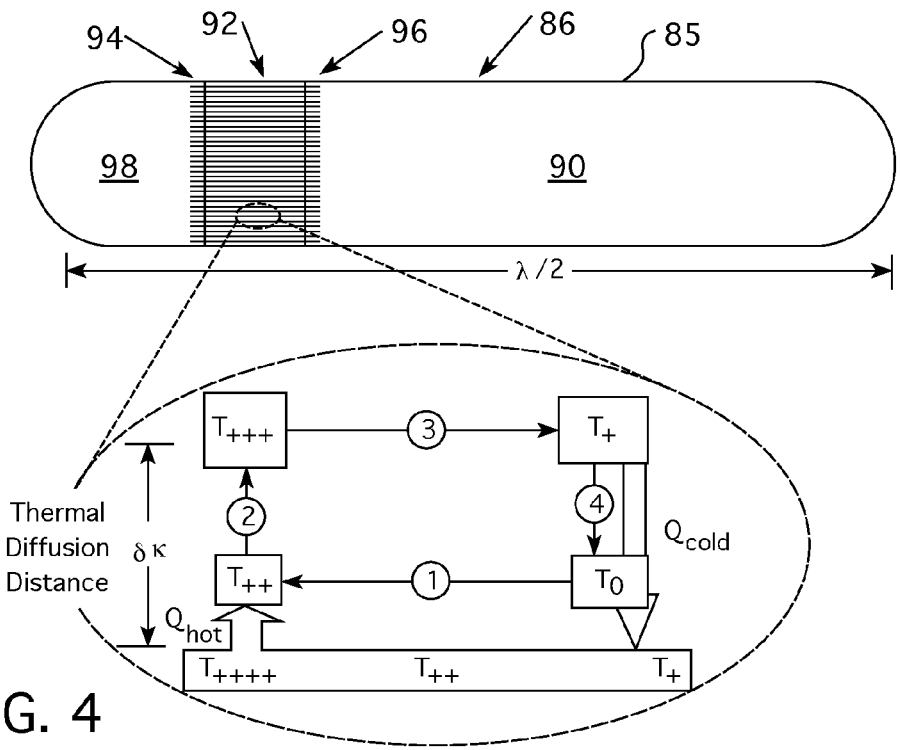
FIG. 4
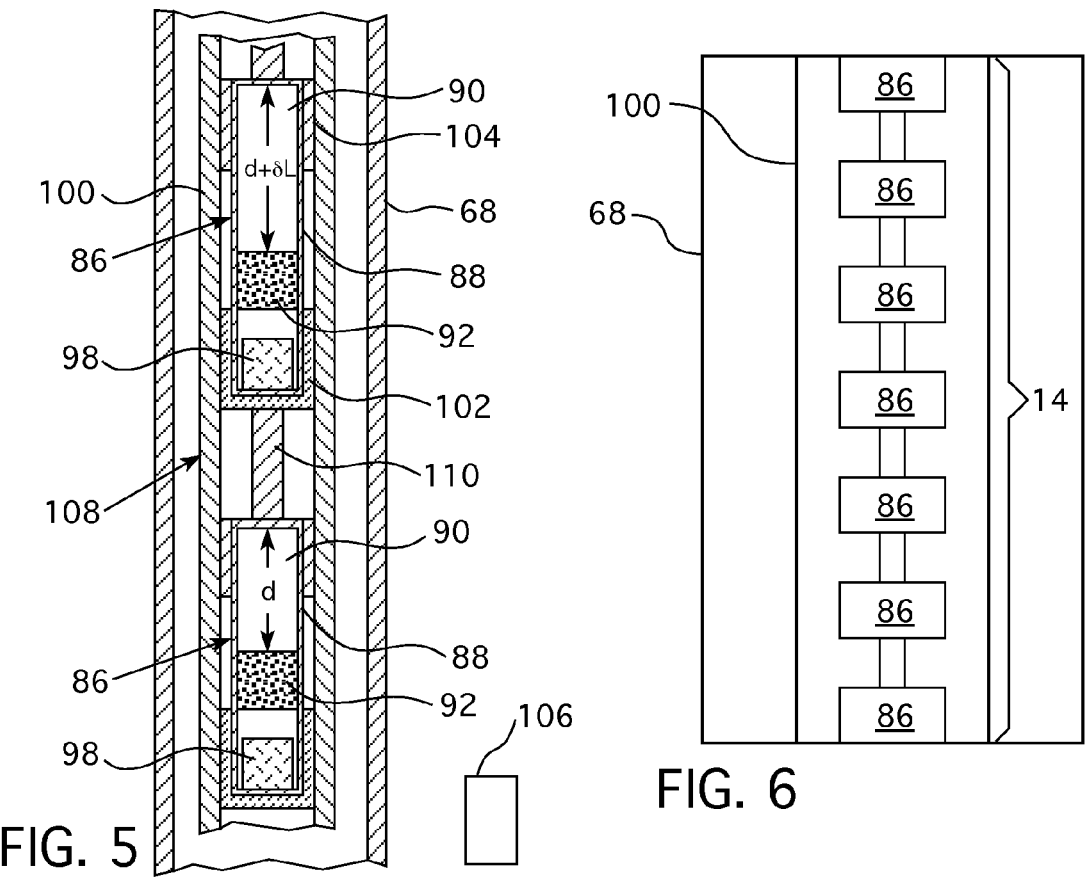
FIG. 5
FIG. 6

THERMO-ACOUSTIC NUCLEAR POWER DISTRIBUTION MEASUREMENT ASSEMBLY

CROSS REFERENCE TO RELATED APPLICATION

This application is a continuation-in-part application of and claims priority to U.S. patent application Ser. No. 13/869,159, filed Apr. 24, 2013, entitled THERMO-ACOUSTIC NUCLEAR POWER DISTRIBUTION MEASUREMENT ASSEMBLY.

BACKGROUND

1. Field

This invention pertains generally to nuclear reactor monitoring systems and more particularly to an in-core power distribution monitor.

2. Related Art

The primary side of nuclear reactor power generating systems which are cooled with water under pressure comprises a closed circuit which is isolated in heat exchange relationship with a secondary circuit for the production of useful energy. The primary side comprises the reactor vessel enclosing a core internal structure that supports a plurality of fuel assemblies containing fissile material, the primary circuit within heat exchange steam generators, the inner volume of a pressurizer, pumps and pipes for circulating pressurized water; the pipes connecting each of the steam generators and pumps to the reactor vessel independently. Each of the parts of the primary side comprising a steam generator, a pump, and a system of pipes which are connected to the vessel form a loop of the primary side.

For the purpose of illustration, FIG. 1 shows a simplified nuclear reactor primary system, including a generally cylindrical reactor pressure vessel 10 having a closure head 12 enclosing a nuclear core 14. A liquid reactor coolant, such as water, is pumped into the vessel 10 by pump 16, through the core 14 where heat energy is absorbed and is discharged to a heat exchanger 18, typically referred to as a steam generator, in which heat is transferred to a utilization circuit (not shown), such as a steam driven turbine generator. The reactor coolant is then returned to the pump 16, completing the primary loop. Typically, a plurality of the above-described loops are connected to a single reactor vessel 10 by reactor coolant piping 20.

An exemplary reactor design is shown in more detail in FIG. 2. In addition to the core 14 comprised of the plurality of parallel, vertical, co-extending fuel assemblies 22, for purposes of this description, the other vessel internal structures can be divided into the lower internals 24 and the upper internals 26. In conventional designs, the lower internals' function is to support, align and guide core components and instrumentation as well as direct flow within the vessel. The upper internals restrain or provide a secondary restraint for the fuel assemblies 22 (only two of which are shown for simplicity in FIG. 2), and support and guide instrumentation and components, such as control rods 28. In the exemplary reactor shown in FIG. 2, coolant enters the reactor vessel 10 through one or more inlet nozzles 30, flows down through an annulus between the vessel and the core barrel 32, is turned 180° in a lower plenum 34, passes upwardly through a lower support plate 37 and a lower core plate 36 upon which the fuel assemblies are seated and through and about the assemblies. In some designs, the lower support plate 37 and the lower core plate 36 are replaced by a single structure, a lower core support plate having the same elevation as 37. The coolant flow through the core and surrounding area 38 is typically large on the order of 400,000 gallons per minute at a velocity of approximately 20 feet per second. The resulting pressure drop and frictional forces tend to cause the fuel assemblies to rise, which movement is restrained by the upper internals including a circular upper core plate 40. Coolant exiting the core 14 flows along the underside of the upper core plate 40 and upwardly in a plurality of perforations 42. The coolant then flows upwardly and radially to one or more outlet nozzles 44.

The upper internals 26 can be supported from the vessel or the vessel head and include an upper support assembly 46. Loads are transmitted between the upper support assembly 46 and the upper core plate 40, primarily by a plurality of support columns 48. Essentially, each of the support columns is aligned above a selected fuel assembly 22 and perforations 42 in the upper core plate 40.

Rectilinearly moveable control rods 28, which typically include a drive shaft 50 and a spider assembly 52 of neutron poison rods, are guided through the upper internals 26 and into aligned fuel assemblies 22 by control rod guide tubes 54. The guide tubes are fixedly joined to the upper support assembly 46 and the top of the upper core plate 40. The support column 48 arrangement assists in retarding guide tube deformation under accident conditions which could detrimentally affect control rod insertion capability.

FIG. 3 is an elevational view, represented in vertically shortened form, of a fuel assembly being generally designated by reference character 22. The fuel assembly 22 is typically used in a pressurized water reactor and has a structural skeleton which, at its lower end, includes a bottom nozzle 58. The bottom nozzle 58 supports the fuel assembly 22 on the lower core plate 36 in the core region of the nuclear reactor. In addition to the bottom nozzle 58, the structural skeleton of the fuel assembly 22 also includes a top nozzle 62 at its upper end and number of guide tubes or thimbles 84 which align with the guide tubes 54 in the upper internals. The guide tubes or thimbles 84 extend longitudinally between the bottom and top nozzles 58 and 62 and at opposite ends are rigidly attached thereto.

The fuel assembly 22 further includes a plurality of transverse grids 64 axially spaced along and mounted to the guide thimbles 84 and an organized array of elongated fuel rods 66 transversely spaced and supported by the grid 64. The grids 64 conventionally formed from an array of orthogonal straps that are interleaved in an egg-crate pattern with the adjacent interface of four straps defining approximately square support cells, many of which support the fuel rods 66 in a transverse, spaced relationship with each other. The remaining cells are occupied by the control rod guide thimbles 84 and an instrument thimble 68. As shown in FIG. 3, the instrument tube or thimble 68 is located in the center of the fuel assembly and extends between and is captured by the bottom and top nozzles 58 and 62. With such an arrangement of parts, fuel assembly 22 forms an integral unit capable of being conveniently handled without damaging the assembly of parts.

As mentioned above, the fuel rods 66 in the array thereof in the assembly 22 are held in spaced relationship with one another by the grids 64 spaced along the fuel assembly length. Each fuel rod 66 includes a plurality of nuclear fuel pellets 70 and is closed at its opposite ends by upper and lower end plugs 72 and 74. The pellets 70 are maintained in a stack by plenum spring 76 disposed between the upper end plug 72 and the top of the pellet stack. The pellets 70, composed of fissile material, are responsible for creating the reactive power of the reactor. The cladding which surrounds the pellets functions as a barrier to prevent the fission by-products from entering the coolant and further contaminating the reactor system.

To control the fission process, a number of control rods 78 are reciprocally moveable in the guide thimbles 84 located at predetermined positions in the fuel assembly 22. Specifically, a rod cluster control rod mechanism 80, positioned above the top nozzle 62 supports a plurality of the control rods 78. The control mechanism has an internally threaded cylindrical hub member 82 with a plurality of radially extending flukes or arms 52 that form the spider previously noted with regard to FIG. 2. Each arm 52 is interconnected to a control rod 78 such that the control rod mechanism is operable to move the control rods vertically in the guide thimbles 84 to thereby control the fission process in the fuel assembly 22, under the motive power of a control rod drive shaft 50 which is coupled to the control rod hub 80 all in a well-known manner.

Movement of the control rods is used to shape the axial and radial power distribution to maintain the peak fuel rod cladding temperatures within acceptable limits. To monitor this process, and to provide information for the control and protection systems, in-core neutron monitors for monitoring the neutron radiation and thermocouples for monitoring the core exit temperature are provided in a number of the fuel assemblies, within the instrument thimbles 68. The signal leads from these sensors have typically been routed, at first through the bottom of the reactor vessel and more recently through the upper internals, exiting through the reactor vessel head, to a control center. However, the top mounted instrumentation complicates the refueling process, because these sensors have to be removed from the core before the fuel assemblies can be accessed for relocation or replacement. The withdrawal of the instrumentation from the core and the later replacement of the instrumentation after the fuel assemblies in the core have been reconfigured adds significantly to the time required to complete the refueling process which typically is on the critical path of an outage. Conserving outage time to a utility operator is a critical objective, because of the high cost of replacement power incurred during an outage.

Accordingly, it is an object of this invention to provide a mechanism for monitoring the axial and radial distribution of the power within the core that will not be required to be removed during a refueling outage, Additionally, it is an object of this invention to provide such a sensor arrangement that can be installed in a majority if not all of the fuel assemblies without creating an obstruction to coolant flow within the upper internals, Further, it is an object of this invention to supply such a sensor system that can be manufactured as an integral part of the fuel assembly.

SUMMARY

These and other objects are achieved by a thermo-acoustic nuclear power distribution measurement assembly having a plurality of thermo-acoustic engines supported in a spaced tandem array and sized to fit within an instrument thimble in a nuclear fuel assembly. Substantially each of the plurality of thermo-acoustic engines has an outer cladding with a self-sustaining heat source supported within an interior of the cladding within the vicinity of one end and separated from a resonant chamber at the other end with a heat exchanger stack separating the heat source from the resonant chamber. The cladding is sized to loosely fit within the instrument thimble to enable coolant to flow around an outside of the surface of the cladding. Each of the resonant chambers are designed to generate a different frequency of sound whose amplitude is representative of the difference in temperature between a first location within the resonant chamber substantially at the heat exchanger stack and a second location substantially at the other end of the cladding. The cladding around the resonant chamber is highly thermally conductive to coot the gas within the chamber. A spacer is interposed between each of an adjacent pair of the thermo-acoustic engines.

Preferably, a portion of the cladding that surrounds the self-sustaining heat source is thermally insulated and the spacers are configured to thermally insulate the heat source of one of an adjacent pair of thermo-acoustic engines from the second of the pair of thermo-acoustic engines. In one embodiment, the self-sustaining heat source of at least some of the pluralities of thermo-acoustic engines is supported at a lower end of the cladding and comprises fissile material. In another embodiment the self-sustaining heat source comprises a material with a high propensity for converting fission gamma radiation into sensible heat, such as tungsten. Desirably, an acoustic telemetry system is provided for receiving the sound generated by substantially each of the plurality of thermo-acoustic engines, at a remote location. Preferably, the spaced tandem array of the plurality of thermo-acoustic engines substantially span a height of a nuclear fuel assembly instrument thimble. In one embodiment, the tandem array of the plurality of thermo-acoustic engines comprises approximately seven thermo-acoustic engines.

The invention also contemplates a nuclear power generating system incorporating a plurality of such spaced tandem arrays of thermo-acoustic engines wherein at least one of the spaced, tandem array of thermo-acoustic engines is located respectively within a plurality of instrument thimbles within the fuel assemblies within the core of the nuclear power generation system. Preferably, one of the spaced tandem array of thermo-acoustic engines is located within the instrument thimble within each of the fuel assemblies within the core that does not receive a control rod. Desirably, one of the spaced tandem array of thermo-acoustic engines is located in each of the instrument thimbles within the core.

BRIEF DESCRIPTION OF THE DRAWINGS

A further understanding of the invention can be gained from the following description of the preferred embodiments when read in conjunction with the accompanying drawings in which:

FIG. 4 is a schematic diagram demonstrating the thermo-acoustic principles employed in this invention;

FIG. 5 is a schematic view of a partial thermo-acoustic nuclear power distribution measurement assembly of one embodiment of this invention; and FIG. 6 is a block diagram of an array of seven thermo-acoustic heat engines.

DESCRIPTION OF THE PREFERRED EMBODIMENT

Figure 1:
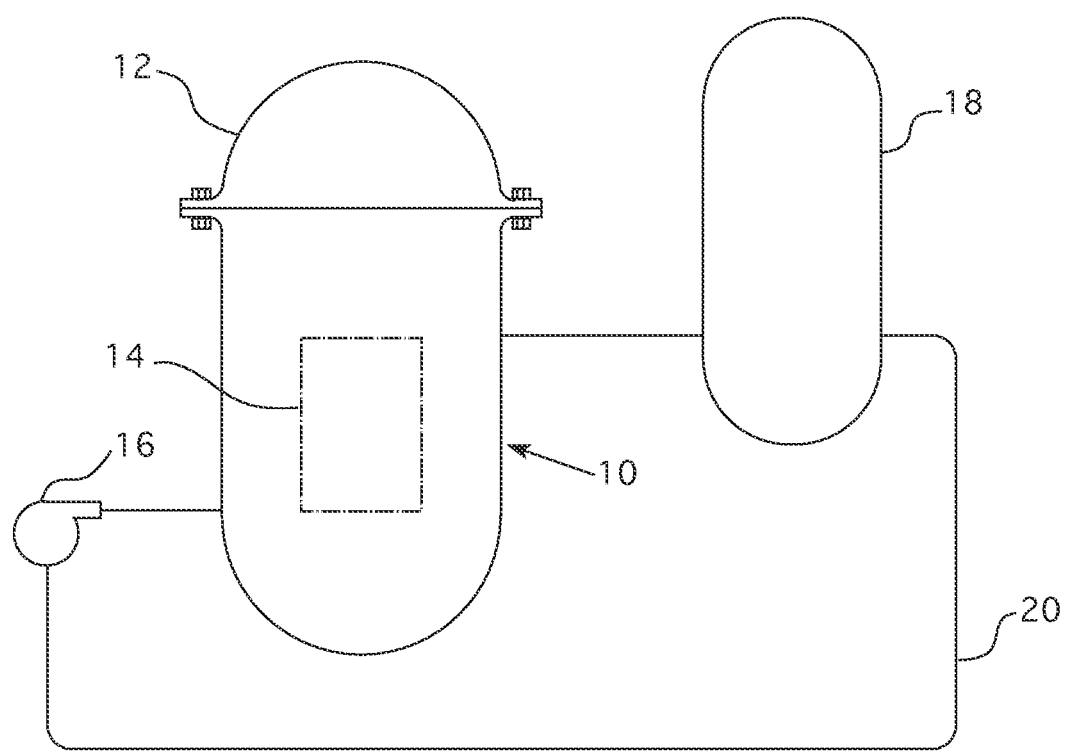
FIG. 1 is a schematic representation the primary side of a nuclear power generating system.
Figure 2:
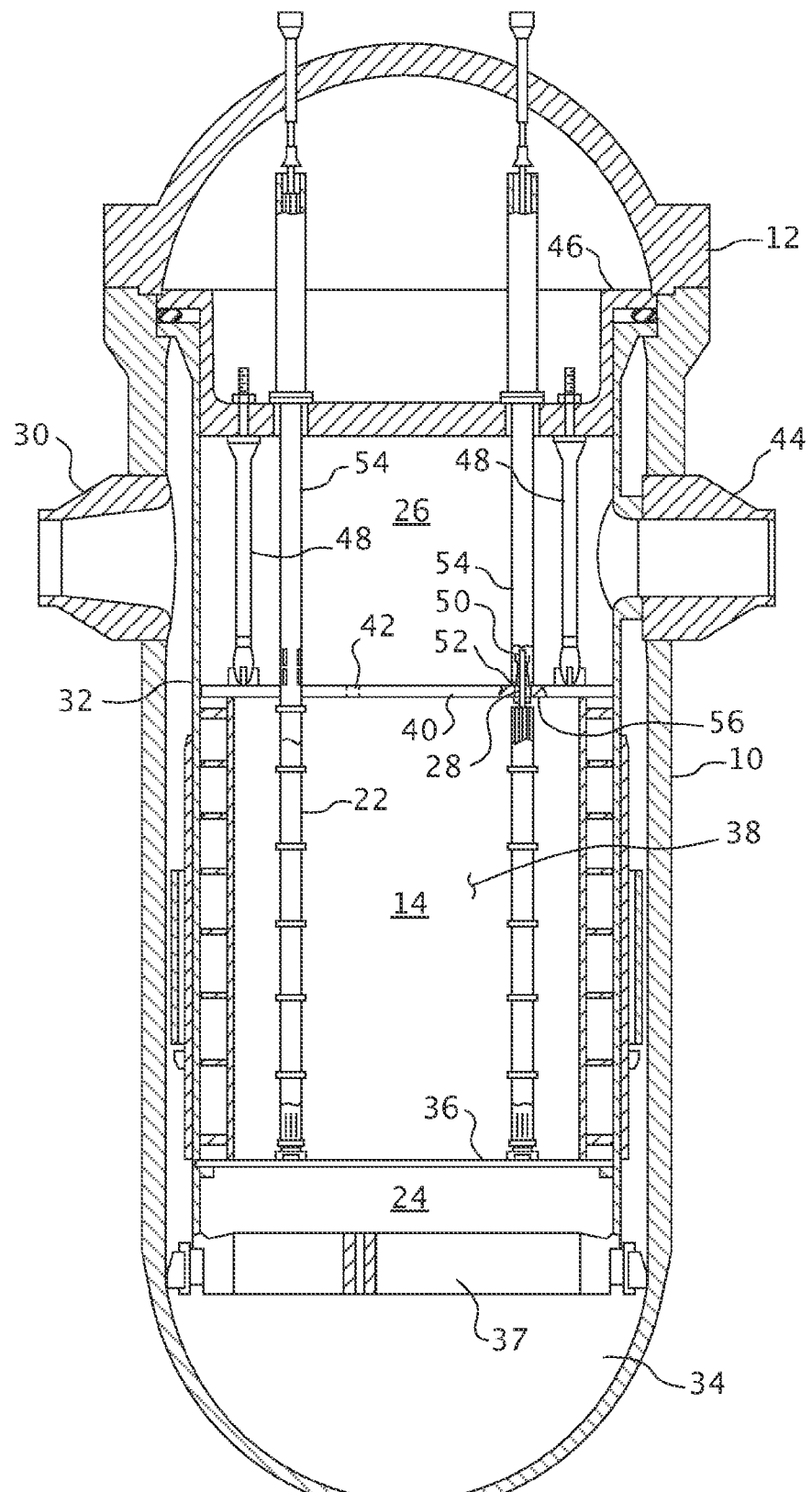
FIG. 2 is an elevational view, partially in section, of a nuclear reactor vessel and internal components to which the embodiments described hereafter can be applied.
Figure 3:
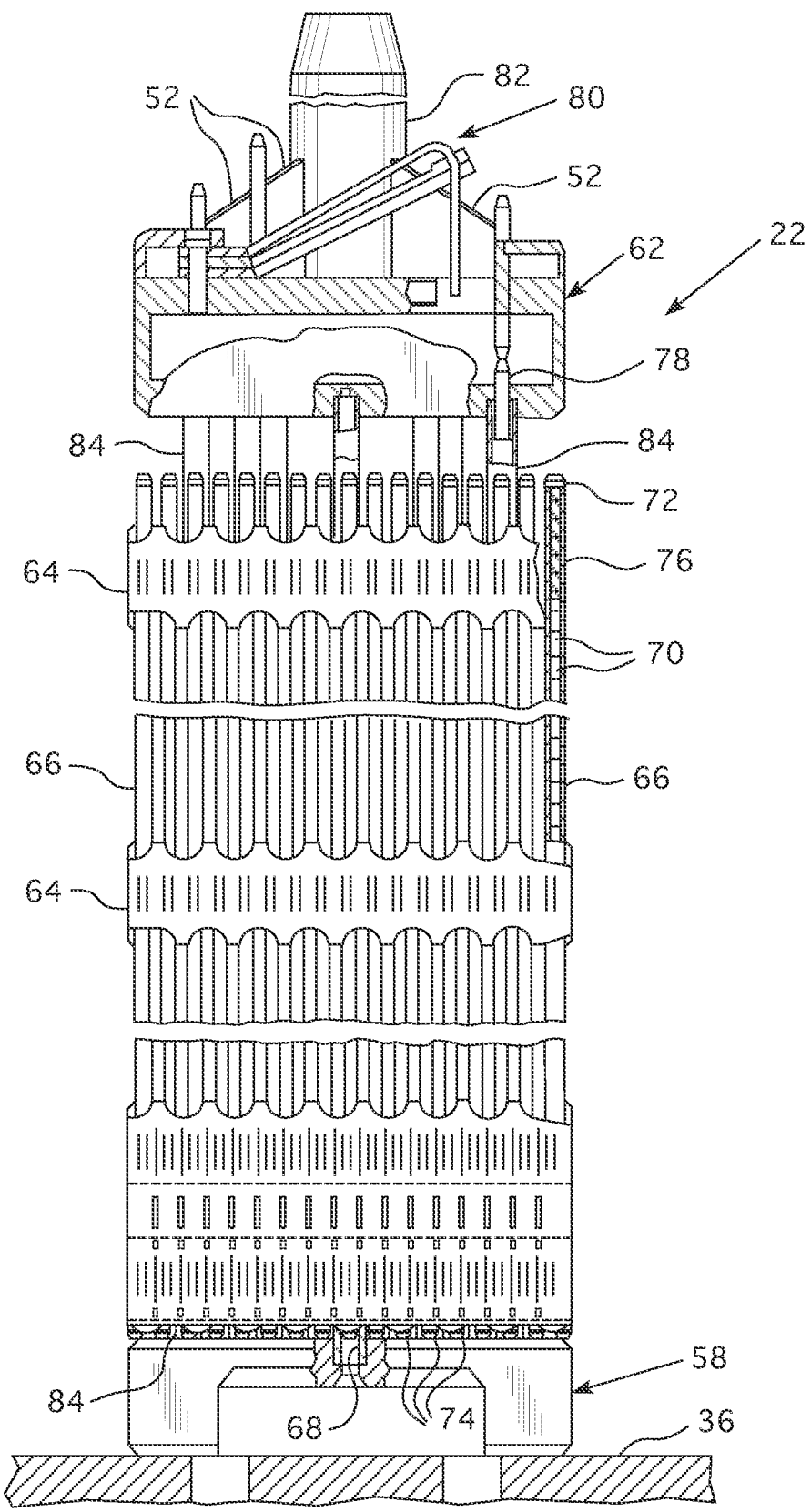
FIG. 3 is an elevational view, partially in section, of a fuel assembly illustrated in vertically shortened form, with parts broken away for clarity.

The performance of a nuclear reactor, like that of many other energy conversion devices, is limited by the temperature which component materials will tolerate without failure. In the case of a nuclear reactor with the core comprising an assemblage of fuel assemblies, such as the one illustrated in FIG. 3, the upper limit of temperature is determined by the fuel rod or fuel pin cladding materials employed. In order to adequately protect the reactor core against excessive temperatures, it is necessary to examine the temperature of the "hottest" fuel pin or the "hottest" coolant channel between adjacent fuel pins in the core, since damage will most likely first occur in the hottest fuel pin. Thus, the "hottest" pin or channel becomes the limiting factor for safe reactor core operation.

As is well known, heat is generated in a reactor by a fission process in the fuel material. The fission process, however, produces not only heat but radioactive isotopes which are potentially harmful and which must be prevented from escaping to the environment. To this end, the fuel is clad with the material which retains the fission products. In order to prevent clad overheating and in the interest of precluding release of fission products which would occur on clad damage or failure, coolant is circulated through the reactor core. Heat transferred to the circulating coolant from the fuel elements is extracted in the form of usable energy downstream of the reactor core in a steam generator as previously mentioned. Thus, for example, in a pressurized water reactor system, the water flowing through the core is kept under pressure, superheated within the core, and is pumped to the tube side of the steam generator where its heat is transferred to water on the shell side of the steam generator. The water on the shell side is under lower pressure and thus, the thermal energy transferred causes the secondary water to boil. The steam so generated is employed to drive a turbine which in turn motors a generator for the production of electricity.

As coolant circulates through the reactor core, heat will be transferred to it either through sub-cooled convection, often referred to as film conduction, or through nucleate boiling. Nucleate boiling occurs at higher levels of heat flux and is the preferred mode of heat removal since it permits more energy to be transferred to the coolant, thereby permitting the reactor to operate at higher levels of efficiency. Nucleate boiling is characterized by the formation of steam bubbles at nucleation sites on the heat transfer surfaces. These bubbles break away from the surface and are carried into the main coolant stream. If the bulk coolant enthalpy is below saturation, the steam bubbles collapse with no net vapor formation in the channel. This phenomenon is called sub-cooled boiling or local boiling. If the bulk fluid enthalpy is at or above the enthalpy of saturated liquid, the steam bubbles do not collapse and the coolant is said to be in bulk boiling.

If the heat flux is increased to a sufficiently high volume, the bubbles formed on the heat transfer surface during nucleate boiling are formed at such a high rate that they cannot be carried away as rapidly as they are generated. The bubbles then tend to coalesce on the heat transfer surface and form a vapor blanket or film. This film imposes a high resistance to heat transfer and the temperature drops across the film can become very large even though there is no further increase in heat flux. The transition from nucleate boiling to film boiling is called "departure from nuclear boiling" (DNB).

Another condition which requires protective action is the occurrence of high local power density in one of the fuel pins. An excessive local power density initiates center line fuel melting which may lead to a breach of the fuel clad integrity. In addition, a condition of excessive local power density is unacceptable in the event of a loss of coolant accident since excessive lower power density would cause the clad temperature to exceed allowable limits if the coolant were lost. As the result of analysis of loss of coolant accidents, values are established by the reactor designers for the maximum allowable local power densities at the inception of a loss of coolant accident, such that the criteria for acceptable consequences are met. The maximum local power density limit is generally specified as a linear power density (LPD) limit with units of watts per centimeter.

A third condition which acts as an operating limit is the licensed power at which the particular reactor is permitted to run. All three of these limiting conditions for operation must be monitored in order to make reactor operations safe. Since clad damage is likely to occur because of the decrease in heat transfer coefficient and the accompanying high clad temperatures which may result when DNB occurs, or because of an excessive local power density, the onset of these conditions must be sensed or predicted and corrective action in the form of a reduction in fission rate promptly instituted. One way of monitoring DNB in the reactor is to generate an index or correlation which indicates the reactor's condition with respect to the probability of the occurrence of DNB. This correlation is called the Departure from Nuclear Boiling Ratio (DNBR). Both the DNBR and LPD limits are indicative of the proximity of operation to the appropriate design limits.

In a complex process, such as nuclear power plant, numerous sensors are provided to measure various physical conditions in the process, such as for example, pressures, temperatures, flows, levels, radiation, and the state of various components, such as, the position of valves, control rods and whether a pump is operating or not. These measurements are generally used to perform three different functions: process control, surveillance and protection. Process control involves automatic or semi-automatic regulation of process conditions to achieve the desired result. Surveillance encompasses monitoring of process conditions to determine that the desired results are being achieved. Protection is concerned with automatic response to abnormal conditions in the process to prevent the operating conditions from exceeding predetermined design limits and to take steps to mitigate the adverse effects of operation outside of the design limits. In the case of a nuclear plant in particular, the protection function is the most demanding of the three. However, all of these functions rely upon the reactor's sensors to be effective. One of the principal sensor systems employed for each of these functions is the in-core neutron sensors which transmit a direct measure of axial and radial power distribution, both during operation and shutdown.

One of the lessons taught by the Fukushima Daichi tsunami was that monitoring the condition of the nuclear fuel is as important during shutdown as it is during operation, especially when there is a loss of on-site and off-site power. This invention employs thermo-acoustic principles to monitor the in-core power distribution and transmit the monitored signals to a remote site without external power and external signal leads that would otherwise encumber the reactor internals and form an impediment to the refueling process. Thermo-acoustic engines (sometimes called "TA engines") are thermo-acoustic devices which use high amplitude sound waves to pump heat from one place to another or conversely use a heat difference to induce high amplitude sound waves. This invention employs the latter principle.

FIG. 4 figuratively illustrates a thermo-acoustic heat engine 86 enclosed within an outer cladding 88. The interior of the cladding 88 is segregated by a heat exchanger 92 also known as a stack, into a heat source 98 and a resonator 90. Heat is applied to the hot side of the heat exchanger 94 and creates a temperature gradient across the stack 92. The cold side of a heat exchanger 96 maintains the temperature of the rest of the engine at a desired value below the temperature of the heat source 98. Though the heat source 98 is shown at one end in FIG. 5 it should be appreciated that the heat source may be spaced from the end of the cladding so long as the heat source 98 is on one side of the heat exchanger stack 92 and the resonator 90 is on the other side of the stack 92. The thermo-acoustic process can be initiated by a perturbation such as background noise or thermal fluctuations. Referring to the block diagram representation at the bottom of FIG. 4 it can be seen that as gas moves within the stack to the left (step 1), heat is transferred from the hot end of the stack 94 to the gas during step 2, increasing the gas temperature from ($T_{++}$ to $T_{+++}$) and pressure. The pressure increase pushes the gas back by a little more each cycle. When the gas moves to the right (step 3), heat is transferred from the gas to the stack (step 4), lowering the gas temperature from $T_+$ to $T_0$ and lowering its pressure. This sucks the gas back toward the hot end of the stack by a little more each cycle. This action within the stack causes the formation of a standing acoustic wave in the resonator portion of the device with a frequency dictated by the length of the device and an amplitude determined by the temperature difference between the hot end and the cold end of the stack. Eventually, the amplitude of the sound wave grows to a steady state level where the acoustic power dissipated during each cycle is equal to the acoustic power generated by the thermo-acoustic process. The result is that an acoustic pressure wave is sustained within the engine. The frequency is related to the length of the resonator L and the sound speed c of the gas within the resonator. In the fundamental half wave length mode, f equals c/2L; for a resonator of uniform cross section the speed of sound is related to the gas's temperature. If this principle is applied within a nuclear core, a thermo-acoustic heat engine can be used to produce standing sound waves with characteristics directly determined by the difference between the heat input to one end and the heat removed at the other end of the thermo-acoustic device.

The heat differential between the two ends of a thermo-acoustic device required to produce useful acoustic energy information, as described above, is extremely difficult to back fit into existing nuclear reactor fuel designs. The measure of the power distribution inside the core of a commercial nuclear reactor using thermo-acoustic principles is made possible using the thermo-acoustic nuclear power distribution measurement assembly claimed hereafter, an embodiment of which is set forth below. This invention allows the core radial and axial power distribution to be determined from sensors that produce sound frequency information corresponding to the radial and axial position inside the reactor core with an amplitude proportional to the magnitude of the neutron flux at the sensor location. The heat input is provided by the inclusion of a self-sustaining heat source such as a fissionable material pellet at the heat input end 98 of each sensor inside the assembly. The term "self-sustaining" is intended to cover any heat source that when placed in the environment of an operating reactor core, will continuously produce sufficient heat to establish the delta-temperature required to generate the temperature gradient needed to produce a practical amount of acoustic energy that can be detected outside the reactor vessel. This allows the relative reactive power at the various sensor locations to be determined. The thermo-acoustic operating principles of the sensor assembly allow this invention to produce instantaneous core power distribution information without requiring an input from an external power source and without signal output cables that require reactor vessel penetrations.

Thus, thermo-acoustic principles described above with regard to FIG. 4 may be used to produce standing sound waves with characteristics directly determined by the difference between the heat input to one end 94 and the heat removed at the other end 96 and the length of the resonator chamber 90. One embodiment of the detector assembly design contemplated by this invention is shown in FIG. 5 and contains a number of thermo-acoustic detector elements 86 that are stacked inside a tube 100 that serves as an outer sheath. The sensor assembly 108 is installed inside the central instrument thimble 68 inside an existing style of commercial fuel assembly 22, such as the one illustrated in FIG. 3. The number and axial position of the detector elements 86 placed inside the outer sheath 100 is determined to achieve the reactor core axial and radial power distribution measurement accuracy required to achieve target core peaking factor and reactor operating power goals. A spacer 110 is interposed between each adjacent pair of the thermo-acoustic detector elements 86. A typical axial spacing will be such that the center of each pellet of fissionable material is located at multiples of one seventh of the active axial fuel region height. Desirably, this device should be placed in all fuel assemblies—including those radial core locations with fuel assemblies containing control rods, which typically do not have fixed in-core flux detectors that are accessed front the upper internals. Thus, employing this concept not only gives a more accurate picture of core axial and radial power distribution, it also eliminates the refueling steps required to withdraw and reinsert the in-core instrumentation.

While only two elements, i.e., thermo-acoustic engines 86, are shown in FIG. 5, it should be appreciated that additional elements can be added in tandem and stacked just as the two elements are shown in FIG. 5, only as an extension of the axial chain of elements 86. The heat source 98 for producing the standing acoustic wave is generated by the fissile material 98 contained in the "hot" end 94 of each device in the assembly 108. The heat will be directly proportional to the fission rate in the fissile material. Therefore, the amplitude, i.e., the loudness, of the wave produced in each device 86 will be proportional to the fission rate at the device location. The delta-temperature required to generate the temperature gradient needed to produce a practical amount of acoustic energy is obtained by covering the hot end of the device with insulation 102 and providing enhanced thermal contact with the coolant at the cool end of the stack in each sensor using, for example, radially projecting fins 104 to enhance coolant surface contact. In accordance with the principles developed here, each device will have a resonator chamber 90 with a unique length so that each device will have a unique frequency to allow the fission rate at each sensor location to be clearly identified from the acoustic wave that the chamber generates. The use of acoustic telemetry 106 is required to collect the sensor signals at a remote location and produce the local fission rate information. The local fission rate information can be used to produce both a total core power and a three-dimensional core power distribution measurement on an essentially continuous, real-time basis using tools currently available and understood by those skilled in the art.

The thermo-acoustic operating principles of the sensor assembly allow this invention to produce instantaneous core power distribution information without requiring an external power source or signal cables that need reactor vessel penetrations and have to be managed during a refueling process.

A further improvement can be obtained employing, as a self-sustaining heat source, a material with a high propensity for converting fission gamma radiation into sensible heat, such as Tungsten, at the heat input end of the sensor inside the assembly in lieu of fissile material. The term "sensible heat" is intended to cover the quantity of heat, i.e., required to generate the temperature gradient needed to produce a practical amount of acoustic energy to be detected outside of the reactor vessel. The key difference between this embodiment and the previous embodiment is that the fissionable material is replaced with a volume of material that will absorb fission gamma radiation energy and convert the absorbed energy to heat that will provide the motive force used to generate sound with an amplitude proportional to the heat input that can be detected outside of the reactor vessel. This type of heat source will not deplete with increasing time inside the reactor core. This will allow a much simpler determination and maintenance of the relationship between heat generation in the heating element and the amplitude of the measured sound. Since the fission gamma population, and the associated heat generated in the heat element material, e.g., Tungsten, is proportional to the local fission rate, the relative reactor power at the sensor location can be determined from the amplitude of sound generated, Tungsten is just one example of a suitable material for this application. A small volume of Tungsten will heat rapidly in the presence of a strong gamma radiation field. A simple calculation for a 0.75 inch (1.9 cm) by 0.75 inch (1.9 cm) by 1 inch (2.54 cm) volume of Tungsten in an operating reactor at full power will produce at least forty Watts of heat. This is more than sufficient to drive suitable sound amplitudes over all necessary frequencies. This embodiment will not require any fissionable material and will not experience any complex changes in operating characteristics as a function of operating time in the reactor. This embodiment will also be much less expensive to manufacture and will ultimately produce a much more stable and accurate core power distribution measurement.

Acoustic sensors can be attached to the outside of the reactor vessel to measure the sound amplitude for each frequency corresponding to a different core axial and radial position. This information may then be used to create 3-D core power distribution using techniques familiar to those skilled in the art, such as the techniques used in the BEACON software system, available from Westinghouse Electric Company LLC, Cranberry Township, Pa.

Thus, the Thermo-Acoustic operating principles of the sensor assembly allow this invention to produce instantaneous core power distribution information inside current reactor designs without requiring external power or signal cables that need reactor vessel penetrations. The implementation of this invention will allow the complete elimination of all current core power distribution measurement systems used in all pressurized water reactors, boiling water reactors liquid metal reactors and high temperature gas reactor designs. It will prove more cost effective to install these sensor assemblies inside every fuel assembly or fuel channel in the reactor core without the need for associated reactor vessel penetrations, associated in-vessel sensor guide path hardware, electrical cables, and associated maintenance activities during refueling. For a back-fit of this sensor system, existing equipment may either be removed or left in place based on the economic factors most favorable to the operator.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. A thermo-acoustic nuclear power distribution measurement assembly comprising:
 a plurality of thermo-acoustic engines supported in a spaced tandem array and sized to fit within an instrument thimble in a nuclear fuel assembly along an axial length of the fuel assembly;
 wherein said plurality of thermo-acoustic engines include at least one pair of thermo-acoustic engines;
 wherein each thermo-acoustic engine of the plurality of thermo-acoustic engines includes an outer cladding, a self-sustaining heat source, a resonant chamber and a heat exchanger stack;
 wherein the cladding is sized to fit within the instrument thimble to enable coolant to flow around an outside surface of the cladding;
 wherein the cladding surrounds the heat source, the resonant chamber and the heat exchanger stack;
 wherein the cladding includes a cladding interior;
 wherein the cladding interior includes one end and another end;
 wherein the heat source is supported within the cladding interior at a first side of the heat exchanger stack facing the one end;
 wherein the resonant chamber is located within the cladding interior at a second side of the heat exchanger stack facing the another end;
 wherein the heat source is separated from the resonant chamber;
 wherein the heat exchanger stack is located within the cladding interior;
 wherein the heat exchanger stack separates the heat source from the resonant chamber;
 wherein each respective resonant chamber of the plurality of thermo-acoustic engines is configured to generate a sound having a frequency that differs from every other respective resonant chamber of the plurality of thermo-acoustic engines;
 wherein for each respective resonant chamber, the sound frequency generated by the respective resonant chamber allows that respective resonant chamber to be uniquely identified from the other respective resonant chambers of said plurality of thermo-acoustic engines;
 wherein for each respective resonant chamber, a difference in temperature between:
  a first location which is within the respective resonant chamber on the second side of the heat exchanger stack and
  a second location which is on the first side of the heat exchanger stack that is heated by the heat source, wherein the second side is opposite the first side; and
  causes the respective resonant chamber to generate a sound with a frequency which comprises an amplitude,
 wherein the amplitude generated corresponds to the difference in temperature between the first location and the second location,
 wherein the amplitude generated also corresponds to a nuclear power level at an axial location of the respective resonant chamber;
 wherein a portion of the cladding that surrounds the resonant chamber is thermally conductive; and
 a spacer interposed between the thermo-acoustic engines of each pair of thermo-acoustic engines.

2. The thermo-acoustic nuclear power distribution measurement assembly of claim 1 wherein a portion of the cladding that surrounds the self-sustaining heat source is thermally insulated.

3. The thermo-acoustic nuclear power distribution measurement assembly of claim 1 wherein the spacers are configured to thermally insulate the heat source of a first engine of a pair of the thermo-acoustic engines from a second engine of the pair of thermo-acoustic engines.

4. The thermo-acoustic nuclear power distribution measurement assembly of claim 1 wherein the self-sustaining heat source of at least some of the plurality of thermo-acoustic engines is supported within a portion of a lower end of the cladding.

5. The thermo-acoustic nuclear power distribution measurement assembly of claim 1 and further including an acoustic telemetry system, wherein the acoustic telemetry system is configured to have acoustic sensors receive at a location outside of a nuclear reactor vessel, sound generated by substantially each respective engine of the plurality of thermo-acoustic engines, when the thermo-acoustic nuclear power distribution measurement assembly is positioned within the nuclear reactor vessel during operation of a corresponding reactor power generation system.

6. The thermo-acoustic nuclear power distribution measurement assembly of claim 1 wherein the spaced tandem array of the plurality of thermo-acoustic engines is configured to substantially span a height of a nuclear fuel assembly instrument thimble.

7. The thermo-acoustic nuclear power distribution measurement assembly of claim 6 wherein the tandem array of the plurality of thermo-acoustic engines comprises seven thermo-acoustic engines.

8. The thermo-acoustic nuclear power distribution measurement assembly of claim 1 wherein the self-sustaining heat source comprises fissile material.

9. The thermo-acoustic nuclear power distribution measurement assembly of claim 1 wherein the self-sustaining heat source is formed from a material operable to convert fission gamma radiation into a quantity of heat that is able to cause the resonant chamber to generate the different frequency of sound with the amplitude.

10. The thermo-acoustic nuclear power distribution measurement assembly of claim 9 wherein the self-sustaining heat source comprises Tungsten.

11. A nuclear power generation system comprising:
a nuclear reactor having a core;
a plurality of nuclear fuel assemblies supported within the core, at least some of the fuel assemblies have an instrument thimble having an axial length that spans a height of the corresponding fuel assembly;
a thermo-acoustic nuclear power distribution measurement assembly positioned within at least some of the instrument thimbles, the thermo-acoustic nuclear power distribution measurement assembly comprising:
a plurality of thermo-acoustic engines supported in a spaced tandem array and sized to fit within an instrument thimble in a nuclear fuel assembly along the axial length;
wherein said plurality of thermo-acoustic engines include at least one pair of thermo-acoustic engines;
wherein each thermo-acoustic engine of the plurality of thermo-acoustic engines includes an outer cladding, a self-sustaining heat source, a resonant chamber and a heat exchanger stack;
wherein the cladding is sized to fit within the instrument thimble to enable coolant to flow around an outside surface of the cladding;
wherein the cladding surrounds the heat source, the resonant chamber and the heat exchanger stack;
wherein the cladding includes a cladding interior;
wherein the cladding interior includes one end and another end;
wherein the heat source is supported within the cladding interior at the one end;
wherein the resonant chamber is located within the cladding interior at the another end;
wherein the heat source is separated from the resonant chamber;
wherein the heat exchanger stack is located within the cladding interior;
wherein the heat exchanger stack separates the heat source from the resonant chamber;
wherein each respective resonant chamber of the plurality of thermo-acoustic engines is configured to generate a sound having a frequency that differs from every other respective resonant chamber of the plurality of thermo-acoustic engines;
wherein for each respective resonant chamber, the sound frequency generated by the respective resonant chamber allows that respective resonant chamber to be uniquely identified from the other respective resonant chambers of said plurality of thermo-acoustic engines;
wherein for each respective resonant chamber, a difference in temperature between:
a first location which is within the respective resonant chamber on the second side of the heat exchanger stack, and
a second location which is on the first side of the heat exchanger stack that is heated by the heat source,
wherein the second side is opposite the first side; and
causes the respective resonant chamber to generate a sound with a frequency which comprises an amplitude;
wherein the amplitude generated corresponds to the difference in temperature between the first location and the second location,
wherein the amplitude generated also corresponds to a nuclear power level at an axial location of the respective resonant chamber;
wherein a portion of the cladding that surrounds the resonant chamber is thermally conductive; and
a spacer interposed between the thermo-acoustic engines of each pair of thermo-acoustic engines.

12. The nuclear power generation system of claim 11 wherein a portion of the cladding that surrounds the self-sustaining heat source is thermally insulated.

13. The nuclear power generation system of claim 11 wherein the spacers are configured to thermally insulate the heat source of a first engine of a pair of the thermo-acoustic engines from a second engine of the pair of thermo-acoustic engines.

14. The nuclear power generation system of claim 11 wherein the self-sustaining heat source of at least some of the plurality of thermo-acoustic engines is supported within a portion of a lower end of the cladding.

15. The nuclear power generation system of claim 11 and further including an acoustic telemetry system, wherein the acoustic telemetry system is configured to have acoustic sensors receive at a location outside of a nuclear reactor vessel, sound generated by substantially each respective engine of the plurality of thermo-acoustic engines, when the thermo-acoustic nuclear power distribution measurement assembly is positioned within the nuclear reactor vessel during operation of a corresponding reactor power generation system.

16. The nuclear power generation system of claim 11 wherein the spaced tandem array of the plurality of thermo-acoustic engines is configured to substantially span a height of a nuclear fuel assembly instrument thimble.

17. The nuclear power generation system of claim 16 wherein the tandem array of the plurality of thermo-acoustic engines comprises seven thermo-acoustic engines.

18. The nuclear power generation system of claim 11 wherein the nuclear reactor has a plurality of control rods that are configured to be inserted into and withdrawn out of at least some of the fuel assemblies and each of the fuel assemblies that does not receive a control rod has one of the thermo-acoustic nuclear power distribution measurement assemblies positioned within its instrument thimble.

19. The nuclear power generation system of claim 18 wherein one of the thermo-acoustic nuclear power distribution measurement assemblies is located in each of the instrument thimbles within the core.

20. The nuclear power generation system of claim 11 wherein the self-sustaining heat source comprises fissile material.

21. The nuclear power generation system of claim 11 wherein the self-sustaining heat source is formed from a material operable to convert fission gamma radiation into a quantity of heat that is able to cause the resonant chamber to generate the different frequency of sound with the amplitude.

22. The nuclear power generation system of claim 21 wherein the self-sustaining heat source comprises Tungsten.

\* \* \* \* \*